(12) United States Patent
Rinkel et al.

(10) Patent No.: US 7,471,759 B2
(45) Date of Patent: Dec. 30, 2008

(54) METHOD FOR ESTIMATING THE SCATTERED RADIATION IN X-RAY TOMOGRAPHY

(75) Inventors: Jean Rinkel, San Francisco, CA (US); Jean-Marc Dinten, Lyons (FR)

(73) Assignee: Commissariat A l'Energie Atomique, Paris (FR)

( * ) Notice: Subject to any disclaimer, the term of this patent is extended or adjusted under 35 U.S.C. 154(b) by 0 days.

(21) Appl. No.: 11/672,729

(22) Filed: Feb. 8, 2007

(65) Prior Publication Data

US 2007/0189439 A1 Aug. 16, 2007

(30) Foreign Application Priority Data

Feb. 10, 2006 (FR) .................................. 06 50489

(51) Int. Cl.
*G01N 23/083* (2006.01)
(52) U.S. Cl. .............................. 378/7; 378/18; 378/98.4
(58) Field of Classification Search ...................... 378/7, 378/18, 98.4
See application file for complete search history.

(56) References Cited

U.S. PATENT DOCUMENTS

| 5,615,279 | A | * | 3/1997 | Yoshioka et al. ............. 382/131 |
| 5,905,809 | A | * | 5/1999 | Timmer ....................... 382/131 |
| 6,134,297 | A | * | 10/2000 | Chao ........................ 378/98.12 |
| 6,256,367 | B1 | * | 7/2001 | Vartanian ...................... 378/7 |
| 6,639,964 | B2 | * | 10/2003 | Schneider et al. ............. 378/7 |
| 6,816,564 | B2 | * | 11/2004 | Charles et al. ................ 378/5 |
| 7,145,980 | B2 | * | 12/2006 | Sakaguchi et al. ............. 378/7 |
| 2007/0086560 | A1 | * | 4/2007 | Kia et al. ..................... 378/7 |

FOREIGN PATENT DOCUMENTS

| EP | 1 566 771 A1 | 8/2005 |
| FR | 2 843 802 | 2/2004 |

OTHER PUBLICATIONS

Keh-Shih Chuang, et al., "Novel scatter correction for three-dimensional positron emission tomography by use of a beam stopper device", Nuclear Instruments and Methods in Physics Research A, vol. 551, No. 2-3, XP-005095126, Oct. 11, 2005, pp. 540-552.

Siobhan Ozard, et al., "Monte Carlo Validation of a Portal Imager Scatter Dose Model", Proceedings of the 22nd Annual EMBS International Conference, vol. 4, XP-002410478, Jul. 23-28, 2000, pp. 2889-2891.

* cited by examiner

*Primary Examiner*—Chih-Cheng G Kao
*Assistant Examiner*—Thomas R Artman
(74) *Attorney, Agent, or Firm*—Oblon, Spivak, McClelland, Maier & Neustadt, P.C.

(57) ABSTRACT

The method is analytical, involves a single irradiation of the object at a plurality of incidences in order to obtain a first three-dimensional image of the total radiation received by the detector, but a double irradiation of a set of calibration phantoms, such as planar plates, in order to obtain their images of the total radiation and the scattered radiation. The three-dimensional image serves only to precisely evaluate, for each projection of the radiation through the object, the equivalent length of the material of the phantoms in order to obtain a similar scattered radiation. In a known manner, a ratio of scattered radiation layers is then calculated for the object and the phantoms according to the total radiation that they have received, and the scattered radiation of the object is obtained by the radiation scattered by the phantoms, which have been measured, and the ratio.

7 Claims, 3 Drawing Sheets

METHOD FOR ESTIMATING THE SCATTERED RADIATION IN X-RAY TOMOGRAPHY

The subject of this invention is a method for estimating the scattered radiation in X-ray tomography.

Numerous object-imaging methods are based on the attenuation undergone by radiation, which depends on the nature of each portion of the objects. The rays are projected on a two-dimensional detector placed behind the object. The three-dimensional image is obtained by performing a plurality of irradiations of the object at different angles of incidence so as to have an adequate number of measurements, and by using a so-called inversion algorithm to go from the series of two-dimensional images taken by the detector to the desired three-dimensional image.

However, each pixel of the detector receives, in addition to a primary ray projected through the object, radiation scattered by the object and that disrupts the measurement. The scattered radiation, the intensity of which is often high, must be estimated and corrected in order to improve the representation of the object.

A number of methods have been used for this. In one of them, a radiation-absorbing machine consisting of an array of small balls ("beam-stops") separated by known distances is used. The rays that arrive in front of the balls are entirely absorbed, while the others pass without attenuation. When the object to be studied and the absorber are simultaneously placed between the radiation source and the two-dimensional detector, the regions of the detector that are located behind the balls form shadow spots illuminated only by the radiation scattered by the object. We deduce therefrom, by interpolations between the shadow spots, the image of the scattered radiation on the entire surface of the detector. This image is subtracted from the ordinary image, taken in the absence of the absorber, of the object studied. The method provides good results but requires at least another irradiation of the object, which therefore receives a much larger dose, which is detrimental in the current case of examining living beings.

Another way of proceeding consists of arranging two detectors, one behind the other, with the first receiving the full radiation and the second receiving only the primary radiation, owing to collimators, which stop the scattered radiation. Each acquisition of a two-dimensional image by the detector is done a single time unlike in the previous method, so that the object is not subjected to an increase in the irradiation dose. The primary radiation is estimated on the second detector by measuring it in the places that are aligned with a collimator opening and the radiation source, and by applying a correction necessitated by the absorption of the radiation in the first detector. A subtraction of the measurements of the first detector by the primary radiation estimated by the second detector in the same places gives an estimation of the scattered radiation; interpolations between these further complement a two-dimensional image of the scattered radiation. The disadvantage of this way of proceeding is that the installation is costly due to the two detectors.

In another category of methods, calibrations are used to estimate the scattered radiation. Images are taken by using, in the place of the object to be studied, plates or other parts with a simple shape, often called calibration phantoms, preferably made of materials with absorption and scattering properties similar to that of the object. The small-ball (beam-stop) array of the first method is also used for application on the calibration phantoms and successively obtaining primary radiation and scattered radiation images for each calibration phantom. The measurements taken with the object are corrected by a functional using a convolution kernel defined by the calibration results, preferably using the images of a chosen phantom, assumed to most closely resemble the object due to a similarity in their measurements. This method is relatively simple, but involves significant approximations. An example is provided in document US 2005/0078787 A1.

In another category of methods, we work with the voxels of the object and not the projections of the radiation. A Monte Carlo iteration method can be cited, in which, after reconstructing a first three-dimensional image of the object by using the raw measurements, the corresponding scattered radiation is simulated, then subtracted from each of the measurements in order to obtain a first estimation of the primary radiation projections. A second three-dimensional image of the object is reconstructed, and its scattered radiation is again simulated and subtracted from the measurements. The three-dimensional images converge toward the real image of the object by repeating the method, but the calculation time is excessive.

In another method of this second category, the radiation scattered by each of the voxels of a first three-dimensional image of the object is evaluated by an analytical method, then corrected by a factor, and a second image of the object is constructed by subtracting the estimated scattered radiation of the measurements. Unlike the previous method, no new image of the object is sought, and the analytical processing is assumed to give an immediate convergence; however, the calculation time is still high, with poorer results than in the previous method. An example of this method is provided in document US 2005/0185753 A1.

The invention proposed here involves an original combination, including both the application of a convolution functional typical of the projection-by-projection analysis methods, while temporarily dividing the object into voxels, that makes it possible both to estimate the scattered radiation with better precision than the methods using projections, without requiring the long calculation times associated with the methods in which the object is divided into voxels.

In its most general form, the invention relates to a method for estimating the radiation scattered by an object studied using radiation traversing the object and a two-dimensional detector receiving the radiation after it has traversed the object, including image sensing of the object by the detector, by measuring the total radiation, the sum of the scattered radiation and the primary radiation that traversed the object on rectilinear projections; and also image sensing of calibration phantoms through which the radiation has successively traversed by measuring, again, for each phantom, the radiation scattered by the phantom and the total radiation, the sum of the radiation scattered by the phantom and the primary radiation that has traversed the phantom on rectilinear projections; then consisting of choosing one of the phantoms, and extrapolating the radiation scattered by the object from the radiation scattered by the chosen phantom, characterised in that it also includes the steps of: forming a three-dimensional image of the object based on images of the object taken by the detector; attributing respective scattering coefficients of the radiation at each portion of the three-dimensional image; determining, for the projections of the radiation through the object, an image with equivalent lengths of material of the phantoms with regard to a total amount of scattered radiation on the projections; and choosing the phantom according to a similarity in the image with equivalent lengths and a thickness traversed by the radiation for measuring said chosen phantom.

The extrapolation is preferably done by applying, on each of the projections, functionals to the total radiation of the object and to the total radiation of the chosen phantom, in order to calculate a scattering of the radiation by a calculation; and the method also includes steps consisting of obtaining a numerical ratio of the functional on the object and the functional on the chosen phantom, and multiplying the radiation scattered by the chosen phantom by the numeric ratio, for each of the projections.

In a preferred embodiment, the functionals are in the form $F=(\phi_{acquired} \times L)*K$, where F is the simulated scattered radiation, $\phi_{acquired}$ is the total radiation, × is a multiplication operator, L is the image of the equivalent lengths of the object or the equivalent length of the chosen phantom through which the projection passes, * is a two-dimensional convolution operator and K is a kernel for two-dimensional distribution of the radiation scattered by the projection.

The invention will now be described in reference to the figures, which illustrate certain embodiments:

Figure 1:
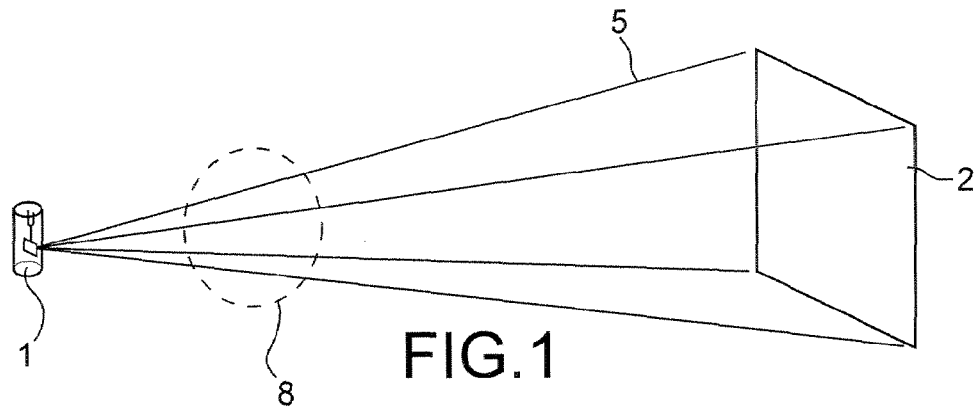
FIG. 1 shows the acquisition of measurements on the object to be studied.
Figure 2:
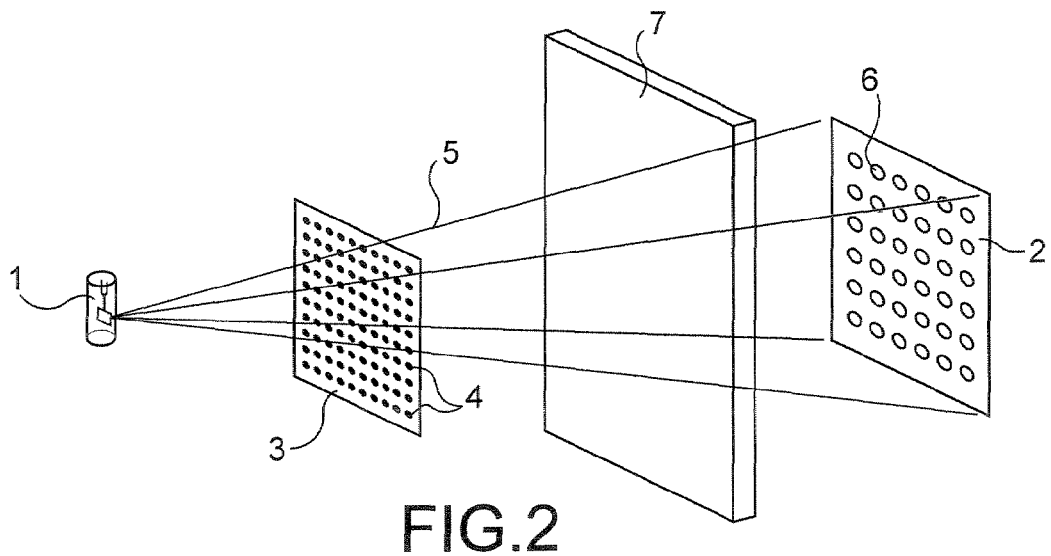
FIG. 2 shows the calibration mode.
Figure 5:
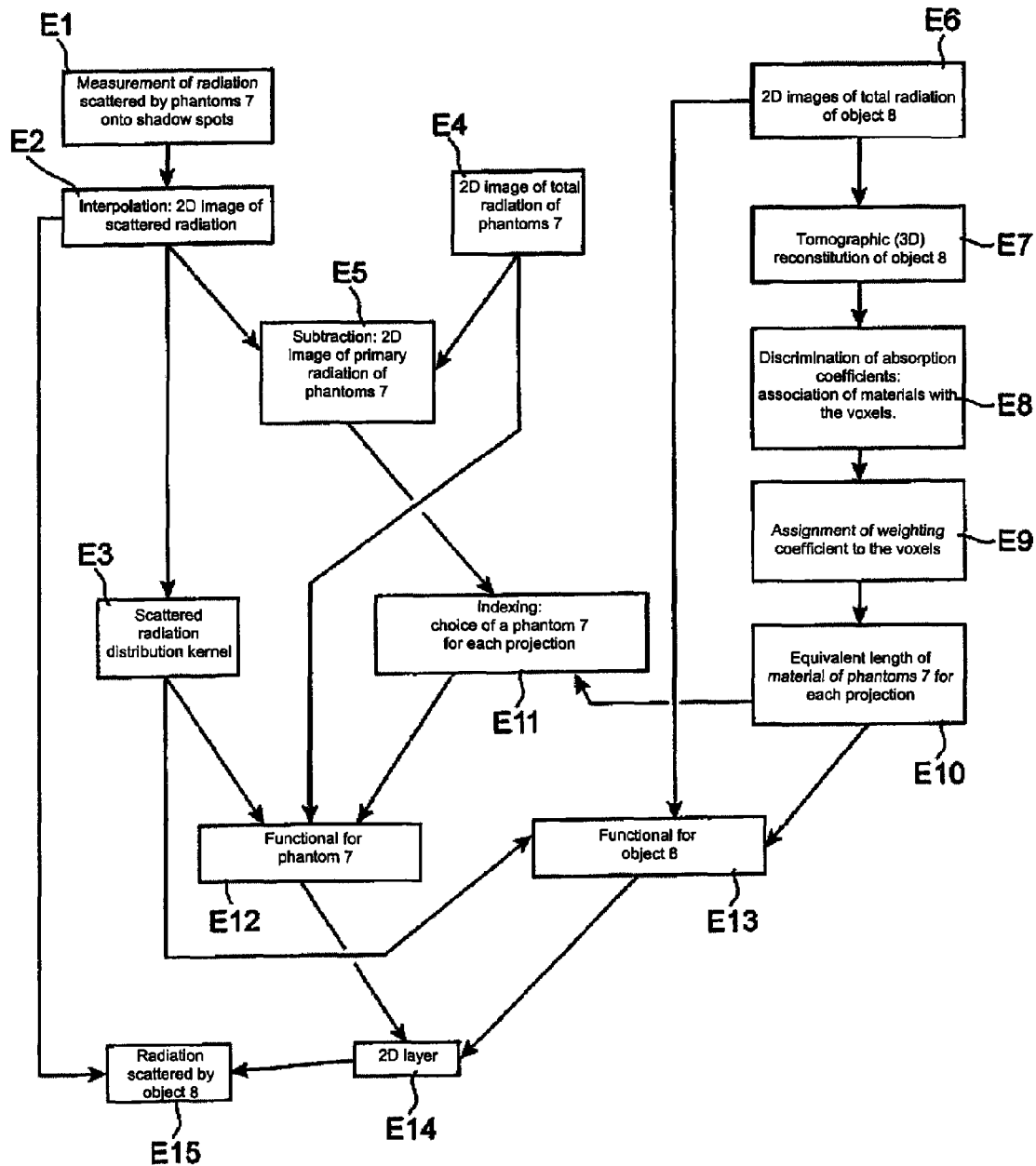
FIG. 5 is a flowchart of the method.

FIG. 2 shows that the apparatus includes a source 1 and a two-dimensional detector 2. An object 8 to be studied is placed between them and attenuates a conical radiation 5 emitted by the source 1 before it reaches the detector 2. The radiation 5 passes through the object 8 by rectilinear projections. The detector 2 measures the attenuation of the radiation on each of the projections. A three-dimensional image of the object may be obtained by rotating, together, the source 1 and the detector 2 around it, and by taking a plurality of two-dimensional images by the detector 2 at different incidences, which are synthesised. In a preliminary step of the method shown in FIG. 1, corresponding to a calibration, the object 8 is however absent and replaced in the same installation by a series of phantoms 7, one of which is shown, and which are studied successively after having been placed in the radiation 5. They are plates or other simple structures made of a homogeneous material, of which the radiation scattering and absorption properties are preferably similar to those of one of the materials that must constitute the object 8 in order to have a good similarity in behaviour. An absorber 3 is also placed in the radiation 5; it is composed of absorbent elements such as balls 4 separated by known distances. The radiation 5 is projected onto the detector 2 with shadow spots 6 corresponding to the projections of the balls 4, where we measure, in the absence of the primary radiation that has traversed the phantom 7 with a rectilinear path and that was completely absorbed by the balls 4, the radiation scattered by the phantom 7 in these places (step E1 of FIG. 5). A complete image of the scattered radiation is obtained by interpolating the measurements taken of the shadow spots 6 on the rest of the span of the detector 2 (step E2). A scattered radiation distribution kernel can be deduced from other measurements taken on this phantom 7 (step E3), possibly by means of other techniques known from the prior art. This distribution kernel expresses the spread of the radiation scattered along a projection on the region surrounding the image. It can often model it by a two-dimensional Gaussian function based on the rays separating the termination point of the projection and each of the points of the surrounding regions, and which depends on a single parameter: the standard deviation.

Another measurement of the phantom 7, with the absorber 3 being removed in this case, makes it possible to obtain another image, which expresses the sum of the primary radiation and the radiation scattered at each pixel of the detector 2 (step E4). The subtraction of the two images at each pixel of the detector 2 then yields an image of the primary radiation alone (E5). The images of the primary radiation, the scattered radiation and the distribution kernel remain associated with the phantom 7. This is repeated for all of the phantoms 7, so as to obtain a calibration catalogue.

The following steps of the method relate to the object 8. A series of two-dimensional images is taken of it in the configuration of FIG. 1 at a plurality of incidences (step E6). A first three-dimensional tomographic reconstruction of the object 8 in voxels is obtained by using any inversion method of the prior art, such as the Feldkamp algorithm (step E7). Each voxel is estimated to undergo radiation, without taking into account that the scattered radiation has disrupted the measurements. The materials constituting the object 8, assumed to be known beforehand, are respectively associated with the voxels by applying threshold criteria according to the known values of the attenuation coefficients of these constituent materials and those that the inversion method has calculated for the voxels (step E8). Weighting coefficients "p", equal to the ratios of the Compton scattering cross-sections of the materials on that of the calibration material (phantoms 7), are assigned to the voxels according to the material associated with each (step E9). For anatomic applications, it is possible to use air, soft tissue and bones as constituent materials.

A two-dimensional image of an equivalent traversed length, $L_{equ}$, is then obtained using the three-dimensional image of the weighting coefficients "p" by applying the formula:

$$L_{equ}(i) = \int_{1=0}^{L(i)} p(1)xdl$$

where L(i) is the real thickness of the object traversed by the primary ray that reaches the detector at the pixel denoted i (step E10). $L_{equ}$ corresponds to the length of each ray of the radiation 5 that must traverse the material of the phantoms 7 to yield the same scattered radiation as in its path in object 8. When $L_{equ}$ of each projection is obtained, the phantom 7 with the thickness closest to the average of $L_{equ}$ on the index zone, is indexed at the projection (step E11). Alternatively, a dummy phantom with a thickness equal to $L_{equ}$ and of which the properties are obtained by interpolation between two real measured phantoms 7, could be indexed at the projection.

A functional F, which gives the high Compton scattering rate of the radiation, is then applied to each measured projection of the indexed phantom 7 (step E12) and the object 8 (step E13). It is defined as:

$$F=(\Phi_{acquired} \times L_{equ})*K$$

for the object 8, where L represents the image of the equivalent lengths calculated on the object, $\phi_{acquired}$ represents the total radiation that has reached the detector 2 for the projection considered, and K represents the scattered radiation distribution kernel. The same functional is applied to the phantom 7 indexed by replacing $L_{equ}$ with the thickness thereof. The application of the functional yields a simulation of the scattering power of the radiation.

The ratio of the functional F of the object 8 on that of the phantom 7 is called a layer and denoted a (obtained in step E14). It is defined for each of the projections and gives the relative scattered radiation of the object 8 with respect to that of the phantom 7. The layer α is then multiplied by the scattered radiation of the phantom 7, insofar as it has been obtained by means of the absorber 3 and the interpolations of the values measured at the shadow spots 6, to obtain an estimation of the scattered radiation of the object 8 on each of the projections (step E15).

The image of the scattered radiation D of the object 8 is thus estimated by the following formula, applied to each of the projections:

$$D = D_{calib} \times \left(\left(\frac{\Phi_{acquired} \times L_{equ}}{\Phi_{calib} \times L_{calib}}\right) * K\right),$$

where $D_{calib}$ is the image of the scattered radiation associated with the phantom 7 with a thickness equivalent to that of the object 8, $\phi_{acquired}$ and $\phi_{calib}$ are the projections of the total radiation received for the object 8 and the phantom 7, $L_{equ}$ and $L_{calib}$ are the image of equivalent lengths of the object 8 traversed by the radiation 5 and the thickness of the phantom 7, and K is the calibrated radiation distribution kernel.

Figure 3A:
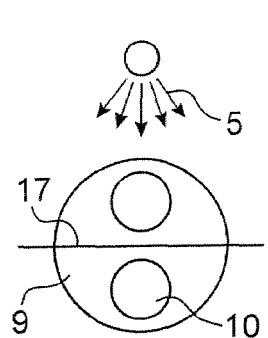
FIGS. 3a and 3b show the representation of an object actually studied in top and side views.
Figure 3B:
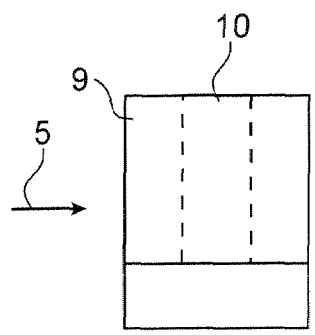
Figure 4A:
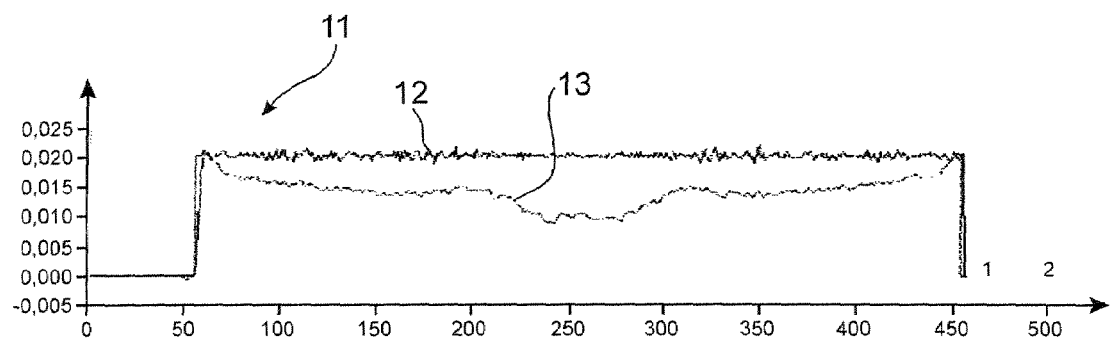
FIGS. 4a, 4b, 4c and 4d show the results of the reconstructions obtained from projections of raw measurements and projections corrected by subtracting the radiation scattered by this object, estimated in three different ways.
Figure 4B:
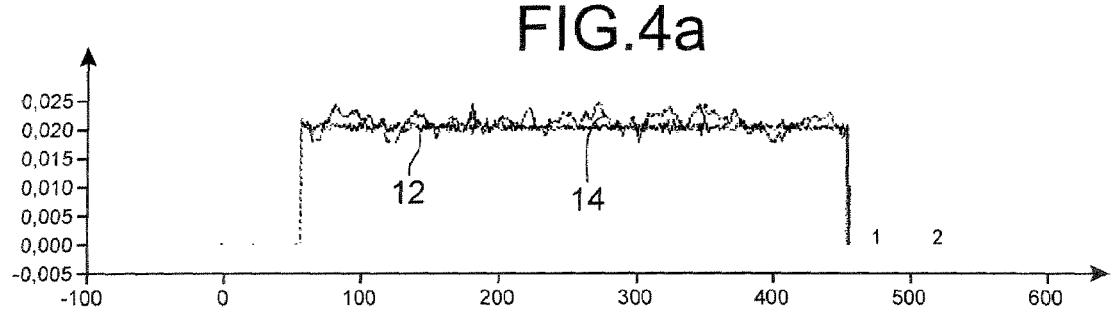

Test results are shown in the following figures. FIGS. 3a and 3b show an object consisting of a Plexiglas cylinder 9 and equipped with two coaxial piercings 10 for air, therefore capable of being compared, for the absorption of the radiation, to the thoracic region and the lungs. FIGS. 4a, 4b, 4c and 4d show results of attenuation of the radiation through the cylinder 9, reconstructions of coefficients based on projections measured in all directions by radiation 5 necessarily occupying a plurality of positions of incidence around the cylinder 9. The reconstruction was performed on a diametral line 17 of the cylinder 9, given on the curve 11 common to all FIGS. 4a and 4b passing between the piercings 10, and therefore involves a plateau 12 corresponding to a homogeneous material. The object is homogeneous; therefore the expected attenuation coefficient profile is a plateau for a radiation 5. FIG. 4a shows the raw attenuation coefficients 13, obtained from measured projections, without correcting the influence of the scattered radiation: the plateau 12 is replaced by a trough shape. FIG. 4b shows the results obtained by performing a second measurement using the absorber 3 for evaluating the scattered radiation, then subtracting it from the total radiation (curve 14): it is seen that the scattered radiation is clearly evaluated, with the estimated attenuation coefficients being similar almost everywhere to the real attenuation coefficients, but at the expense of increased irradiation, as indicated.

Figure 4C:
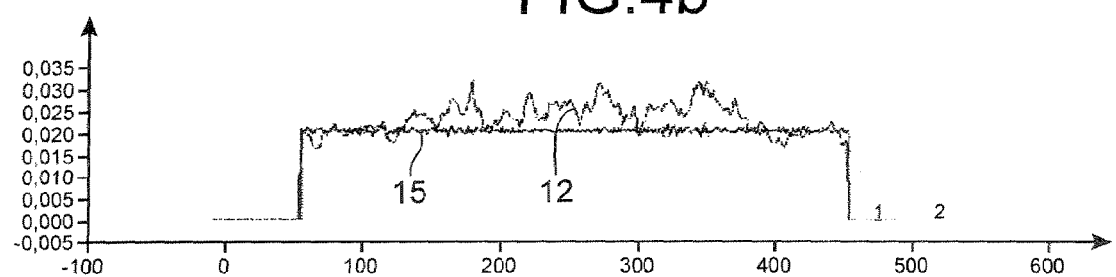

FIG. 4c shows the result obtained according to the method, as described above, of US 2005/0078787 A1 (curve 15): the result is better than that of FIG. 4a, but it is not entirely satisfactory, with the scattered radiation generally being overestimated and variations of reconstructed attenuation coefficients being present in this example.

Figure 4D:
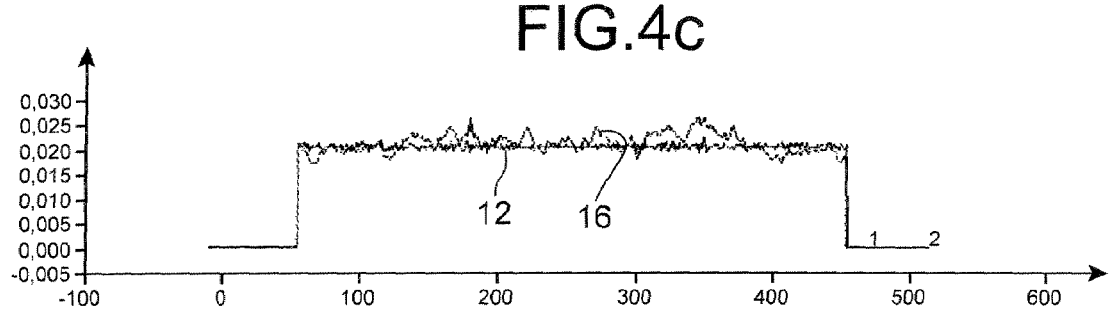

Finally, FIG. 4d shows the use of the invention (curve 16): the results are as good as in the case of FIG. 4b, and without an increase in the dose received.

The invention claimed is:

1. A method for estimating scattered radiation of an object using primary radiation to traverse the object and a two-dimensional detector to receive the primary radiation after the primary radiation has traversed the object, said method comprising:
    image sensing the object using the two-dimensional detector by measuring the total radiation, said total radiation including the sum of the scattered radiation and the primary radiation that has traversed the object on rectilinear projections;
    image sensing a plurality of calibration phantoms successively traversed by a primary phantom radiation by measuring, for each phantom, a total phantom radiation, said total phantom radiation including the sum of scattered phantom radiation and the primary phantom radiation that has traversed the phantom on rectilinear projections;
    choosing at least one of the plurality of calibration phantoms by forming a three-dimensional image of the object based on images of the object taken by the two-dimensional detector, attributing respective scattering coefficients of the radiation of each portion of the three dimensional image, determining, for the projections of the radiation through the object, an image with equivalent lengths of material of the phantoms with regard to a total amount of scattered radiation on the projections, and choosing the phantom according to a similarity of the equivalent length and a thickness traversed by the radiation for measuring said chosen phantom; and
    extrapolating the radiation scattered by the object from the radiation scattered by the at least one chosen phantom.

2. The method for estimating scattered radiation of an object according to claim 1, wherein one of the plurality of phantoms is chosen independently for each of the projections.

3. The method for estimating scattered radiation of an object according to claim 1, further comprising:
    obtaining a numerical ratio of a functional on the object and a functional on the at least one chosen phantom; and
    multiplying the scattered phantom radiation by the numerical ratio, for each of the projections,
    wherein the extrapolating is accomplished by applying, on each of the projections, functionals to the total radiation of the object and to the total phantom radiation of the at least one chosen phantom, in order to calculate a scattering of the radiation by a simulation.

4. The method for estimating scattered radiation of an object according to claim 1, wherein the object is a living being and the scattering coefficients of the three-dimensional image portions are determined by attributing compositions of air, soft tissue or bone to said portions.

5. The method for estimating scattered radiation of an object according to claim 3, wherein the functionals are in the form $F=(\Phi_{acquired} \times L)*K$, where F is the simulated scattered radiation, $\Phi_{acquired}$ is the total radiation, × is a multiplication operator, L is the image of the equivalent lengths of the object or the equivalent length of the chosen phantom through which the projection passes, * is a two-dimensional convolution operator and K is a kernel for two-dimensional distribution of the radiation scattered by the projection.

6. The method for estimating scattered radiation of an object according to claim 2 further comprising:
    obtaining a numerical ratio of a functional on the object and a functional on the at least one chosen phantom; and
    multiplying the scattered phantom radiation by the numerical ratio, for each of the projections,
    wherein the extrapolating is accomplished by applying, on each of the projections, functionals to the total radiation of the object and to the total phantom radiation of the at least one chosen phantom, in order to calculate a scattering of the radiation by a simulation.

7. The method for estimating scattered radiation of an object according to claim 2, wherein the object is a living being and the scattering coefficients of the three-dimensional image portions are determined by attributing compositions of air, soft tissue or bone to said portions.

* * * * *